United States Patent
Pöhlmann et al.

(10) Patent No.: US 9,540,313 B2
(45) Date of Patent: Jan. 10, 2017

(54) METHOD AND APPARATUS FOR PURIFYING NITRATION PRODUCTS

(71) Applicant: JOSEF MEISSNER GMBH & CO. KG, Köln (DE)

(72) Inventors: Jürgen Pöhlmann, Köln (DE); Heinrich Hermann, Köln (DE); Mirko Händel, Neunkirchen-Seelacheid (DE); Jürgen Gebauer, Troisdorf (DE)

(73) Assignee: Josef Meissner GmbH & Co. KG, Köln (DE)

( * ) Notice: Subject to any disclaimer, the term of this patent is extended or adjusted under 35 U.S.C. 154(b) by 0 days.

(21) Appl. No.: 14/632,086

(22) Filed: Feb. 26, 2015

(65) Prior Publication Data

US 2015/0174551 A1 Jun. 25, 2015

Related U.S. Application Data

(62) Division of application No. 14/118,737, filed as application No. PCT/EP2012/002139 on May 18, 2012, now Pat. No. 9,115,048.

(30) Foreign Application Priority Data

May 19, 2011 (DE) .................. 10 2011 102 059

(51) Int. Cl.
*C07C 201/16* (2006.01)
*B01J 19/24* (2006.01)

(52) U.S. Cl.
CPC .............. *C07C 201/16* (2013.01); *B01J 19/24* (2013.01); *B01J 2219/24* (2013.01)

(58) Field of Classification Search
None
See application file for complete search history.

(56) References Cited

U.S. PATENT DOCUMENTS

| | | | |
|---|---|---|---|
| 3,221,064 A | 11/1965 | Edward et al. | |
| 4,482,769 A | 11/1984 | Toseland et al. | |
| 7,470,826 B2 * | 12/2008 | Hermann | C07C 201/16 568/924 |
| 2004/0267061 A1 | 12/2004 | Dieterich et al. | |

* cited by examiner

Primary Examiner — Yong Chu
Assistant Examiner — Ana Z Muresan
(74) Attorney, Agent, or Firm — Edward E. Sowers; Brannon Sowers & Cracraft PC

(57) ABSTRACT

The present invention relates to a method for removing impurities from nitrated crude products obtained during the nitration of nitratable aromatic compounds, after removal of the final nitrating acid, by treatment with a washing medium, and also to a plant or apparatus suitable for implementing this method. Further provided by the invention is a production plant for the nitration of nitratable aromatic compounds with subsequent purification of the nitrated products.

7 Claims, 4 Drawing Sheets

METHOD AND APPARATUS FOR PURIFYING NITRATION PRODUCTS

CROSS-REFERENCES TO RELATED APPLICATIONS

This is a divisional application that claims priority to and the benefit of co-pending U.S. patent application Ser. No. 14/118,737, filed on Nov. 19, 2013, which is a National Stage filing of International Application PCT/EP 2011/002139 filed May 18, 2012, entitled "METHOD AND APPARATUS FOR PURIFYING NITRATION PRODUCTS" claiming priority to German Application No. DE 10 2011 102 059.8 filed May 19, 2011. The subject application claims priority to co-pending application Ser. No. 14/118,737, to PCT/EP 2011/002139, and to German Application No. DE 10 2011 102 059.8, the disclosures of which are incorporated herein by reference.

BACKGROUND OF THE INVENTION

The present invention relates to the technical field of nitration, in particular the preparation of nitrated aromatic organic compounds (hereinafter referred to synonymously as "nitroaromatics", "nitration products" or the like) and their purification after production.

The present invention relates in particular to a process for removing impurities (in particular unreacted starting materials, reaction by-products, nitrating acid and reaction products thereof, e.g. nitrogen oxides or nitrous acid, etc.) from crude nitrated products obtained in the nitration of nitratable aromatic compounds by treating the crude products, after removal of the residual nitrating acid, with a washing medium. In other words, the present invention relates to a process for purifying crude nitrated products obtained in the nitration of nitratable aromatic compounds after removal of the residual nitrating acid.

Furthermore, the present invention relates to an apparatus or plant for removing impurities from crude nitrated products obtained in the nitration of nitratable aromatic compounds after removal of the residual nitrating acid. The apparatus or plant of the invention is, in particular, suitable for carrying out the process of the invention.

Finally, the present invention relates to a production plant for nitrating nitratable aromatic compounds with subsequent purification of the nitrated products.

Aromatic nitro compounds such as nitrobenzene (MNB), mononitrotoluene (MNT), dinitrotoluene (DNT), trinitrotoluene (TNT), nitrochlorobenzene (MNCB), etc., which are prepared by reaction of a corresponding aromatic such as benzene, toluene, xylene, chloro-benzene, dichlorobenzenes, etc., with nitric acid, either directly or in the presence of sulfuric acid catalyst and water-binding agent, have to be subjected before further processing to multistage washing and additional purification steps in order to remove the impurities which are still dissolved or suspended in the crude nitroaromatics, e.g. sulfuric acid, nitric acid, nitrogen dioxide, nitrophenols, nitrocresols, etc., which can be present, for example, as mononitro, dinitro and trinitro compounds, and other oxidation products such as nitrobenzoic acids and degradation products from the decomposition of nitrophenols, or the unreacted aromatics or undesirable isomers, e.g. in the production of TNT, from the crude mixture of nitroaromatics.

The washing of the crude nitroaromatics in order to remove the dissolved and suspended acids of the nitration mixture, the nitrophenols and other acidic impurities which can still be extracted by the washing medium usually consists of three steps (see, for example, F. Meissner et al., Industrial and Engineering Chemistry, Vol. 46, pages 718 to 724 (1954); Ullmanns Enzyklopädie der Technischen Chemie, $4^{th}$ edition, Vol. 17, pages 384 to 386; H. Hermann et al., "Industrial Nitration of Toluene to Dinitrotoluene", ACS Symposium Series 623 (1996), pages 234 to 249, editors: L. F. Albright, R. V. C. Carr, R. J. Schmitt; U.S. Pat. No. 6,288,289 B1; EP 1 816 117 B1). Water is usually used as washing medium with washing usually being carried out as a liquid/liquid wash (i.e. at temperatures at which the nitroaromatic to be washed is present as liquid).

This three-stage wash usually comprises the following steps:

1. An acid wash with water to remove the dissolved and suspended mineral acids, e.g. sulfuric acid, nitric acid and nitrogen dioxide ("acid wash").
2. A basic or alkaline wash in the presence of a base ("alkali wash"), e.g. sodium carbonate (soda), sodium bicarbonate, sodium sulfite, sodium hydrogensulfite, ammonia, sodium hydroxide, potassium hydroxide, etc. (see, for example, U.S. Pat. No. 4,482,769 A, U.S. Pat. No. 4,597,875 A or U.S. Pat. No. 6,288,289 B1), to remove the weakly acidic impurities dissolved in the crude nitroaromatic, e.g. the nitrophenols, nitrocresols, nitrobenzoic acids, degradation products from the oxidative decomposition of the phenols or of aliphatic or cyclic hydrocarbons, etc., e.g. oxalic acid, etc., or the unsymmetrical isomers in the case of TNT ("basic wash").
3. A neutral wash to remove the residual traces of alkali and to further reduce the amount of impurities still remaining in traces in the product ("neutral wash").

The aim of these washing steps is to obtain not only a pure product but also very little wastewater per metric ton of product, where the washed-out impurities are present in the wastewater in such a form that they can be disposed of inexpensively.

To minimize the amounts of water required for this wash, the wash can, for example, be carried out in countercurrent in such a way that the water used for the neutral wash is, after addition of bases, used in the alkali wash (cf., for example, A. B. Quakenbush et al., The Olin Dinitrotoluene (DNT) Process, Polyurethanes World Congress 1993, Publish.: Technomic Lancaster, pages 484 to 488) or that the acid wash is carried out using a minimal amount of water, so that a concentrated acid which can be recirculated either directly or after further concentration to the nitration is obtained.

Thus, EP 0 279 312 B1, EP 0 736 514 B1 and EP 1 780 195 B1 describe processes by means of which the mineral acids still suspended and dissolved in the nitroaromatics after the nitration, e.g. sulfuric acid, nitric acid and nitrogen dioxide, are washed out in a plurality of stages and selectively and are recirculated to the nitration, so that no wastewater is obtained from the acid wash and has to be disposed of.

However, processes in which, in order to minimize the amount of wastewater to be treated, no acid wash is carried out but instead only an alkaline wash and a neutral wash, as described, for example, in Kirk-Othmer, Encyclopedia of Chemical Technology, $4^{th}$ ed., Vol. 17, pages 136 to 138, or in U.S. Pat. No. 4,091,042 A, have also become known.

Apart from minimizing the waste streams, a further aim is to minimize the technical outlay required for the wash (e.g. by the technology used for washing being specifically matched not only to the washing stage but also to the product to be washed).

As washing apparatuses, mixer-settler units (cf., for example, EP 1 593 654 A1) in which the mixing part is usually a stirred vessel (cf., for example, Ullmann's Encyclopedia of Industrial Chemistry, 5$^{th}$ ed., Vol. B 3, pages 6.19 to 6.21; M. Baerns et al., Technische Chemie, Verlag Wiley-VCH 2006, pages 352/352) are usually used in the individual washing stages for washing the nitroaromatics to be purified. Thus, the German patent DE 1 135 425 describes an arrangement of mixers and settlers which allows even nitroaromatics which are crystalline at room temperature, e.g. DNT, TNT or NCB, to be washed in liquid form at elevated temperatures with minimization of the outlay for heating. However, centrifugal pumps and static mixers have also been used as mixers (cf., for example, the documents U.S. Pat. No. 3,221,064 A or EP 1 816 117 B1).

However, the use of the mixer/settler technology (cf., for example, FIG. 1) is complicated and expensive. Due to the unavoidable carryover in the case of continuously operated stirred vessels as mixers, it is, especially in the removal of nitrophenols or nitrocresols when these are present in high concen-trations in the crude nitroaromatic, necessary to work in a number of stages and preferably in countercurrent in order to obtain the low content of impurities which is desired for the further processing of the nitroaromatic (e.g. a content of nitrophenols of less than 10 ppm, preferably from 2 to 3 ppm). A wash in multistage extraction columns is also technically complicated and expensive and not very effective. In addition, the generation of large exchange areas for a two-phase mixture in a short time for effective mass transfer followed by a rapid chemical reaction can be achieved neither in a stirred vessel nor in extraction columns.

J. M. Coulson, F. E. Warner, "A Problem in Chemical Engineering Design: The Manufacture of Mononitrotoluene", a publication by "The Institution of Chemical Engineers", 56, Victoria Street, London S.W.1, 1949, pages 25/26, describes a triple wash of the MNT using a washer of the Holley-Mott (mixer/settler) type, in which the acid wash and the alkaline wash is carried out in countercurrent in at least two stages in order to achieve sufficient removal of the acids and nitrocresols dissolved or suspended in the MNT.

In the Canadian patent CA 1 034 603, a four-stage acid wash in countercurrent is proposed in order to wash out the nitric acid and sulfuric acid dissolved and suspended in the crude DNT.

U.S. Pat. No. 4,091,042 A describes a four-stage wash using sodium carbonate in countercurrent for removing all acidic components from crude nitrobenzene, e.g. entrained sulfuric acid and the dinitrophenols and picric acid dissolved in the nitroaromatic down to 2000 ppm and obtain the desired purity.

EP 1 816 117 A1 describes a four-stage neutral wash in countercurrent using four stirred vessels and the associated separation apparatuses (known as "mixer/settler technology") in order to reduce the still too high content of nitrophenols after the alkaline wash from about 50 ppm to a residual content of about 2 ppm. However, even when the stirred vessels are replaced by centrifugal pumps as mixing devices, three stages are still required to obtain a residual content of nitrophenols in the resulting nitrobenzene of 3 ppm.

U.S. Pat. No. 4,994,242 A discloses that static mixers are not suitable as mixing device in two-phase systems on the industrial scale alone to produce optimal dispersion of the two mutually immiscible phases in one another. Thus, EP 1 816 117 B1 describes the use of a static mixer for the alkaline wash; the nitrobenzene treated therewith still contains more than 50 ppm of nitrophenols which have to be brought down to about 2 ppm by means of a complicated multistage neutral wash.

As has been explained for an acid wash in EP 1 780 195 B1, the washing of nitroaromatics is a complex operation. Apart from generation of a sufficiently large exchange area between organic phase and washing phase (usually water) in order to achieve optimal transition of the impurity to be removed from the organic phase, the effectiveness of a washing stage depends on the partition equilibria of the impurity between organic phase and washing medium and also on whether the impurity extracted from the organic phase is stable as such in the washing medium or is withdrawn from the partition equilibrium by a subsequent reaction.

Thus, nitrogen dioxide reacts with water after transition from the organic phase into the aqueous phase so as to disproportionate into nitric acid and NO according to equation (1):

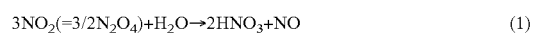
$$3NO_2(=3/2N_2O_4)+H_2O \rightarrow 2HNO_3+NO \tag{1}$$

Both the transition of the nitrogen dioxide from the organic phase, probably as dimer, and also the reaction of the nitrogen dioxide (as $N_2O_4$) with water are comparatively slow reactions compared to a neutralization, so that time is required for removal of the nitrogen dioxide from the organic phase by means of a wash with subsequent chemical reaction.

On the other hand, in the case of acids such as sulfuric acid, nitric acid or the weakly acidic nitrophenols, the dissociation of the acids into hydronium ions and the associated anions which occurs in the washing water (equation 2) or the neutralization which occurs in the presence of alkali (equation 3) is a very rapid process by means of which the washed-out impurities are withdrawn from the partition equilibrium between nitroaromatic and washing water and are then found in anionic form only in the washing water.

$$H_2SO_4+H_2O \rightarrow H_3O^++HSO_4^- \tag{2}$$

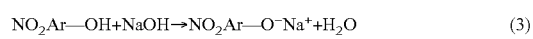
$$NO_2Ar\text{---}OH+NaOH \rightarrow NO_2Ar\text{---}O^-Na^++H_2O \tag{3}$$

As a result of this rapid neutralization of anion-forming materials in the alkaline washing medium, it is to be expected that the extraction of these materials from the organic phase is essentially mass-transfer-controlled and the wash follows essentially the same kinetic laws as a mononitration, e.g. the nitration of benzene to form nitrobenzene.

The processes and plants known from the prior art for purifying crude nitrated products often do not operate with high efficiency or else not in a satisfactory way. Hitherto, excessively complex process sequences or operations have been associated therewith, and the desired purities are often not achieved, at least not with a justifiable outlay.

BRIEF SUMMARY OF THE INVENTION

It is therefore an object of the present invention to provide a process and an apparatus or plant for removing impurities from crude nitrated products obtained in the nitration of nitratable aromatic compounds after removal of the residual nitrating acid, in which the abovementioned problems and disadvantages associated with the prior art are at least largely avoided or else at least reduced in severity.

In particular, it is an object of the present invention to provide a process and an apparatus or plant suitable for carrying out this process by means of which efficient purification of the crude nitrated products as are obtained from the nitration of nitratable aromatic compounds after removal of the residual nitrating acids is made possible.

It is a further object of the present invention to carry out the washing of the crude nitroaromatics which result after removal of the residual nitrating acid, in which significant amounts of impurities such as entrained nitrating acid, dissolved sulfuric acid, nitric acid, nitrogen dioxide, nitrophenols, nitrobenzoic acids, degradation products from the oxidative degradation of nitrophenols, etc., can be present, effectively in a single-stage manner in each washing step in such a way that the nitrophenol content of the washed nitroaromatic is very low (e.g. in the case of nitrobenzene from an adiabatic nitration originally containing about 2000 ppm of dinitrophenols and trinitrophenols, the content of nitrophenols after the alkaline wash is below 50 ppm, preferably below 10 ppm, and after the neutral wash is below 2 ppm) and the outlay and costs are significantly lower than in the case of the previously utilized processes and apparatuses of the prior art.

The abovementioned objects are achieved according to the invention by a process as described herein; further, advantageous further developments and embodiments of the process of the invention are similarly described.

The present invention further provides an apparatus or plant; further, advantageous further developments and embodiments of this aspect of the invention are similarly disclosed.

In addition, the present invention provides a production plant; further, advantageous embodiments and further developments of this aspect are subject matter are provided.

It goes without saying that embodiments, variants, advantages or the like which are referred to below in respect of only one aspect of the invention, to avoid unnecessary repetitions, of course also apply analogously to the other aspects of the invention.

Furthermore, it goes without saying that when values, numbers and ranges are indicated below, the respective values, numbers and ranges indicated do not constitute a restriction; it will be self-evident to a person skilled in the art that the indicated ranges or values can be deviated from in individual cases or for a particular application without going outside the scope of the present invention.

In addition, all values and parameters or the like indicated below can basically be measured or determined by standardized or explicitly indicated methods of determination or else by methods of determination with which a person skilled in this field will be familiar.

This having been made clear at the outset, the present invention will be described in more detail below.

DETAILED DESCRIPTION OF THE INVENTION

Figure 1:
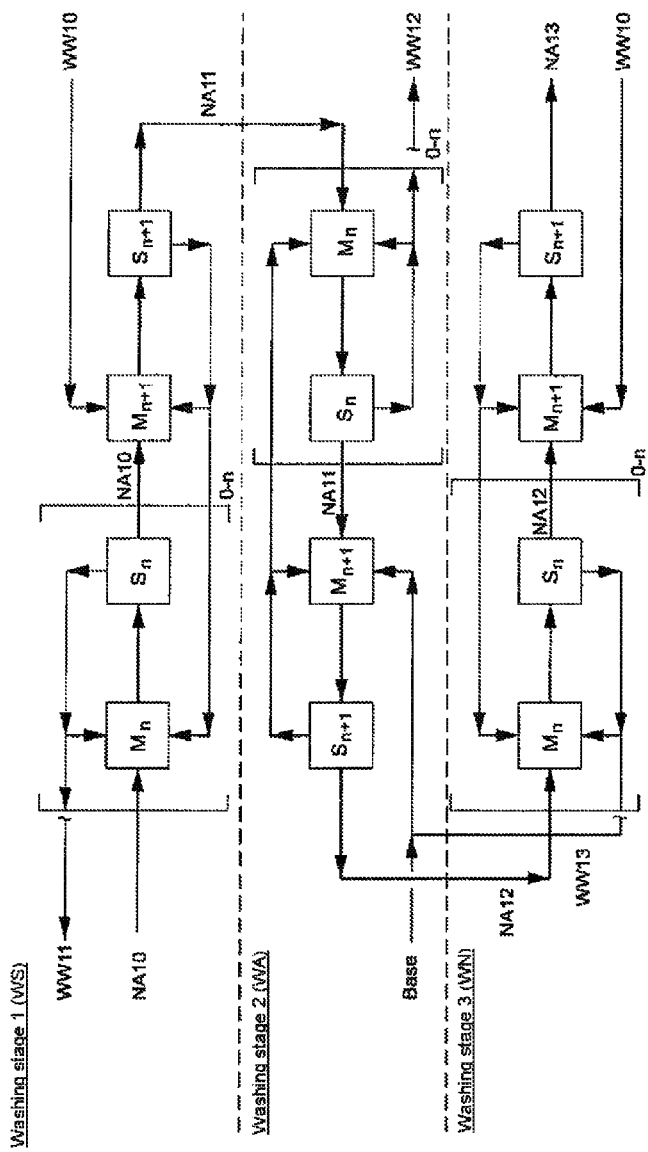
FIG. 1 provides a schematic depiction of a wash of nitroaromatics according to the prior art by means of mixer/settler technology for the usual three washing stages of a wash of nitroaromatics.

The present invention thus provides, according to a first aspect of the present invention, a process for removing impurities from crude nitrated products obtained in the nitration of nitratable aromatic compounds by treating the crude product, after removal of the residual nitrating acid, with a washing medium, wherein the process of the invention comprises the following process steps:

in a first process step (a), the crude nitrated products are firstly brought into contact with a washing medium and the crude nitrated products and the washing medium are dispersed in one another in such a way that a dispersion, in particular an emulsion, results (i.e. in other words, a dispersion or emulsion is produced from crude nitrated products and washing medium in this first process step (a)) and in a second process step (b), the resulting dispersion, in particular emulsion, is subsequently fed into a tube reactor so that the impurities initially present in the crude nitrated products are removed during passage of the emulsion through the tube reactor and/or so that the impurities initially present in the crude nitrated products are transferred into the washing medium or neutralized thereby during passage of the emulsion through the tube reactor.

The process of the invention is thus outstandingly suitable for purifying crude nitrated products obtained in the nitration of nitratable aromatic compounds after removal of the residual nitrating acid.

The principle of the process of the invention therefore consists of firstly bringing the crude nitroaromatics originating from the nitration, which still contain significant amounts of impurities, into contact, after removal of the residual nitrating acid (e.g. in a separator), with a washing medium and converting the mixture of nitroaromatics to be purified and washing medium into an emulsion or dispersion and subsequently feeding the resulting emulsion or dispersion into a tube reactor so that the impurities initially present in the nitroaromatics to be purified are transferred into the washing medium or neutralized thereby, forming a purified nitroaromatic.

As the applicant has discovered, completely surprisingly, the use of a tube reactor in combination with an upstream dispersing or emulsifying device leads to particularly good mixing and particularly intimate and fine dispersion of washing medium and nitroaromatic to be purified being able to be achieved, so that the impurities can in this way be removed completely or at least essentially completely in a single process step (namely in the treatment in the tube reactor).

In contrast to the prior art, further, complex process steps for purifying the crude nitroaromatic are in this way avoided in an efficient manner without a reduction in quality having to be accepted in the purification of the crude nitroaromatic.

The tube reactor used according to the invention for the treatment of the crude nitroaromatic with the washing medium surprisingly ensures such intimate and fine dispersion of the crude nitroaromatic and the washing medium that all or at least essentially all impurities are transferred into the washing medium or neutralized thereby in the treatment in the tube reactor as per process step (b), so that the impurities can subsequently (i.e. after conclusion of process step (b)) be separated off together with the washing medium from the then purified nitroaromatic.

It has surprisingly been found that it is possible in the context of the present invention to carry out washing of nitroaromatics successfully in effect in a single stage, even in the case of high loading with impurities such as nitrating acid, nitrophenols and nitrocresols, by means of a simple and inexpensive combination of jet mixers but also other dispersing devices, e.g. centrifugal pumps, with additional devices such as static mixers, orifice plates, etc., in tube reactors either alone or in combination with stirred vessels which allow a precisely defined mixing energy to be introduced into the mixture of the mutually immiscible phases. The emulsions of the organic phase to be purified in the washing medium (0/W type) or of the washing medium in the organic phase (W/O type) which can be produced in this way produce the interface between nitroaromatic to be washed and washing medium required for effective and optimal mass transfer.

As regards the production of the emulsion or dispersion in process step (a), this is generally carried out by means of a suitable dispersing or emulsifying device, in particular by means of a suitable mixing device.

In the context of the present invention, it is possible to use, for example, a stirred vessel, a jet mixer (or Jet Mixing Device) or a pump, in particular a centrifugal pump, as dispersing or emulsifying device (i.e. in particular as preferably first dispersing or emulsifying device), in particular as mixing device.

In an embodiment of the invention, a pump, in particular a centrifugal pump, is used as dispersing or emulsifying device, in particular as mixing device, in process step (a).

In an alternative embodiment which is preferred according to the invention, a jet mixer (synonymously also referred to as "Jet Mixing Device") is used as dispersing or emulsifying device, in particular as mixing device, in process step (a). The jet mixer used according to the invention is, in particular, a device which produces a (central) driving jet in a medium (e.g. annular jet) surrounding the (central) driving jet.

As jet mixers, it is possible to use all types of jet mixers which allow the nitroaromatic to be washed or the washing medium to be injected at high relative velocity by means of the central driving jet as free jet, which can consist either of the washing medium or of the nitroaromatic to be washed, in such a way that either the nitroaromatic to be washed is dispersed as emulsion having a large interfacial area in the washing medium or the washing medium is similarly dispersed in the nitroaromatic to be washed. Devices of this type are described, for example, in Ullmann's Encyclopedia of Industrial Chemistry, 2003, 5th ed., Vol. B 4, pages 87/88 and 565 to 571, or else in Perry's Chemical Engineers' Handbook, McGraw-Hill Book Company, 1984, $6^{th}$ edition, pages 5-21 to 5-23 or else in the German first publication DE 2 151 206.

Here, the (central) driving jet in the jet mixer can be the washing medium and the surrounding medium can be the crude nitrated aromatic to be purified; as an alternative, however, the (central) driving jet can also be formed by the crude nitrated product to be purified and the medium surrounding the (central) driving jet can be formed by the washing medium. Both alternative embodiments lead to the desired result.

Particularly good results in respect of the purification of the crude aromatic to be purified are (independently of whether the central driving jet is formed by the washing medium or else by the crude nitrated product to be purified) obtained when the ratio of the velocities of the central driving jet and the medium (e.g. annular jet) surrounding the central driving jet in the jet mixer is set in the range from 1:5 to 30:1, preferably in the range from 1:2 to 20:1, particularly preferably in the range from 1:1 to 10:1. Particularly intimate and fine dispersion of washing medium and crude product and consequently particularly efficient purification are achieved in this way.

The flow velocity of the washing emulsion downstream of the jet mixer in the subsequent tube reactor is, in particular, in the range from 0.1 to 15.0 m/s, preferably in the range from 0.5 to 10 m/s.

According to an embodiment of the present invention, the dispersing device, in particular the mixing device, used in process step (a) can be installed upstream, in particular directly upstream, of the tube reactor. According to a particular variant of this embodiment, the dispersing or emulsifying device, in particular the mixing device, can go over into the tube reactor.

However, it is equally possible for the dispersing device, in particular the mixing device, to be integrated into the tube reactor or be a constituent of the tube reactor. For this purpose, the dispersing device can, for example, be arranged in the upper or upstream part of the tube reactor. Such an embodiment is particularly useful when the dispersing device, in particular the mixing device, is configured as a jet mixer.

In an embodiment which is particularly preferred according to the invention, the tube reactor for carrying out process step (b) can be equipped with mixing elements, in particular for the introduction of additional mixing energy; particularly good purification results can be achieved in this way since a further improved, particularly intimate dispersion of washing medium and crude aromatic to be purified is achieved by means of the additional mixing elements. The mixing elements can be, in particular, metal plates, in particular impingement plates or deflection plates, orifice plates, static mixers, flow dividers or the like. According to the invention, it is preferable for from 1 to 15, in particular from 2 to 15, preferably from 2 to 10, particularly preferably from 2 to 5, mixing elements to be present in the tube reactor.

In this embodiment, preference is given to the mixing elements provided in the tube reactor introducing a total mixing energy (i.e. a mixing energy per unit volume) of from 10 to 1000 joule/liter, preferably from 10 to 500 joule/liter, particularly preferably from 20 to 200 joule/liter. In other words, a total mixing energy (i.e. a mixing energy per unit volume) of from 10 to 1000 joule/liter, preferably from 10 to 500 joule/liter, particularly preferably from 20 to 200 joule/liter, is preferably introduced in this embodiment.

Particularly good results are, in particular, also achieved when the mixing elements are configured so that the pressure drop per mixing element is from 0.1 bar to 3.0 bar, preferably from 0.3 to 1.5 bar, particularly preferably from 0.3 to 0.8 bar.

As regards the residence time of the emulsion of washing medium and crude aromatics in the tube reactor in process step (b), this can vary within a wide range. Particular preference is given to the residence time in the tube reactor being from 0.1 to 120 seconds, preferably from 0.1 to 60 seconds, particularly preferably from 1 to 30 seconds. Particularly good washing results are achieved in this way since a sufficient minimum residence time but also an economic throughput are ensured.

In the purification, the mass ratio and phase ratio of crude nitrated products to be purified to washing medium are also important and can each vary within a wide range.

Particularly good results are obtained when the mass ratio of crude nitrated products to be purified to washing medium (i.e. freshly introduced washing medium) is set in the range from 200:1 to 1:10, preferably in the range from 100:1 to 1:5, particularly preferably in the range from 10:1 to 1:2.

Particularly good results are equally obtained when the phase ratio (i.e. in particular the phase ratio in the washing apparatus) of crude nitrated products to be purified to washing medium is set in the range from 25:1 to 1:5, in particular in the range from 10:1 to 1:2, preferably in the range from 5:1 to 1:1. The setting of the phase ratio can, in particular, be effected by circulation of the washing medium after phase separation. This ensures firstly an optimal exchange area between organic phase and washing medium and secondly a very short time for the phase separation in the phase separation apparatus.

The washing of the nitroaromatics is usually carried out as a liquid/liquid wash (i.e. at temperatures at which both the nitroaromatic to be washed and purified and also the washing medium are present as liquids).

As regards the washing medium used according to the invention, this is liquid under process conditions, in particular at temperatures at or above 5° C., in particular at temperatures at or above 25° C., and atmospheric pressure. According to the invention, preference is given to using an aqueous-based washing medium, preferably water.

Depending on the phase ratio in the washing apparatus, the nitroaromatic to be washed is dispersed in the washing medium as an oil-in-water emulsion (O/W emulsion) or the washing medium is dispersed in the aromatic to be washed as a water-in-oil emulsion (W/O emulsion).

The efficiency of the washing medium can be increased by adding at least one base to the washing medium. The base can, in particular, be selected from the group consisting of inorganic hydroxides, carbonates, hydrogencarbonates, sulfites, hydrogen sulfites and ammonia and also mixtures or combinations thereof, preferably from the group consisting of sodium hydroxide, potassium hydroxide, sodium carbonate, potassium carbonate, sodium hydrogencarbonate, potassium hydrogencarbonate, ammonia, ammonium carbonate, sodium sulfite and sodium hydrogen sulfite and also mixtures or combinations thereof.

The amount of alkali used in an alkaline wash should, in particular, be sufficiently high not only for all acids to be able to be converted quantitatively into their salts but, in particular, an excess of base should be used so that the pH of the washing liquor is sufficiently high for even weak acids such as mononitrophenols to be able to be washed out quantitatively.

The content of alkali can be, in particular, from 0.01 mol/l to 0.4 mol/l, preferably from 0.02 mol/l to 0.2 mol/l, but at least twice the amount required for neutralization of all nitrophenols.

Particularly good results are obtained when the content of base in the washing medium is from 0.01 to 0.4 mol/l, preferably from 0.02 to 0.2 mol/l.

In particular, the content of base in the washing medium should be at least twice the amount of alkali which is theoretically required for neutralization of all nitrophenols present as impurities.

As indicated above, the phase ratio of nitroaromatic to be washed to freshly introduced washing medium should advantageously be from 200:1 to 1:10, preferably from 100:1 to 1:5, particularly preferably from 10:1 to 1:2.

Circulation of the washing medium after phase separation makes it possible to set a phase ratio of nitroaromatic to be washed to washing medium in the washing apparatus of from 25:1 to 1:5, in particular from 10:1 to 1:2, particularly preferably from 5:1 to 1:1, in order firstly to produce an optimal exchange area between organic phase and washing medium and secondly to keep the time for the phase separation in the phase separation apparatus as short as possible.

Depending on the phase ratio in the washing apparatus, the nitroaromatic to be washed is dispersed in the washing medium as an oil-in-water emulsion (O/W emulsion) or the washing medium is dispersed in the aromatic to be washed as a water-in-oil emulsion (W/O emulsion) (cf. what has been said above).

Depending on the phase ratio selected, either the aromatic to be washed or the washing medium is used as driving jet in order to set the desired type of emulsion.

The flow velocity of the washing emulsion downstream of the jet mixer in the subsequent tube reactor can be, in particular, in the range from 0.1 to 15.0 m/s, preferably from 0.5 to 10 m/s.

The ratio of the velocity of the central jet to that of the surrounding medium is, as indicated above, in the range from 1:5 to 30:1, preferably from 1:2 to 20:1 and particularly preferably from 1:1 to 10:1.

To prevent the coalescence of the washing emulsion after a short time and thus prevent incomplete extraction of the impurity to be removed from the nitroaromatic to be purified, it is advantageous to keep the washing emulsion stable by additional introduction of mixing energy until all impurities have been washed from the nitroaromatic and re-extraction into the nitroaromatic to be washed is prevented by further reactions in the washing medium. This additional mixing energy can be introduced into the mixture of the two mutually immiscible phases by feeding into a reactor having additional mixing devices, preferably into a tube reactor without backmixing, with the emulsion of the O/W or W/O type being maintained in the tube reactor by means of additional mixing elements distributed over the tube reactor, e.g. orifice plates, deflection plates, baffles, static mixers or other static mixing elements.

Preference is given to from 1 to 15, in particular from 2 to 15, preferably from 2 to 10 and particularly preferably from 2 to 5, mixing elements being present in the tube reactor, with the jet mixer also counting as mixing element.

The total mixing energy per unit volume to be introduced should be from 10 to 1000 J/l, preferably from 10 to 500 J/l and particularly preferably from 20 to 200 J/l.

The pressure drop per mixing element should be from 0.1 to 3.0 bar, preferably from 0.2 to 1.5 bar and particularly preferably from 0.2 to 0.8 bar, in order to keep the number of additional mixing elements required in the tube reactor as low as possible and to keep the residence time in the phase separation apparatus as short as possible.

The residence time in the tube reactor for separating off acids, followed by a fast further reaction such as neutralization, from the nitroaromatic to be washed, e.g. nitric acid, sulfuric acid, mononitrophenols, dinitrophenols and trinitrophenols and cresols, nitrobenzoic acids, etc., in a wash by means of alkali, e.g. sodium hydroxide, sodium carbonate, bicarbonate, ammonia, potassium hydroxide, etc., should be not more than from 0.1 to 120 seconds, preferably from 0.1 to 60 seconds, particularly preferably from 1 to 30 seconds.

To remove impurities from the nitroaromatic to be washed with high partition coefficients in favor of the nitroaromatic to be washed, high mass transfer resistances in the organic phase and slow further reactions of the extracted impurity in the washing medium, e.g. nitrogen dioxide, the residence time in the subsequent reactor should be matched to these circumstances (e.g. by a combination of the above-described devices for producing an optimal washing emulsion with stirred vessels in order to produce the necessary residence time). In a particular embodiment of the process of the invention, this is, in particular, achieved by a combination of the above-described devices for producing an optimal washing emulsion with stirred vessels in order to ensure the necessary residence time for phase transfer and the subsequent reaction.

As indicated above, the amount of alkali used in an alkaline wash should not only be sufficiently high for all acids to be able to be converted quantitatively into their salts but an excess of base should also be used so that the pH of the washing liquor is sufficiently high for even weak acids such as mononitrophenols to be able to be washed out quantitatively. As indicated above, the content of alkali should be, in particular, from 0.01 mol/l to 0.4 mol/l, preferably from 0.02 mol/l to 0.2 mol/l, but at least twice the amount required for neutralization of all nitrophenols.

The emulsion present at the end of the mixing section can, for example, be separated again into the individual phases in a phase separation apparatus (e.g. separator or settler). The washing medium with the impurities present therein can either be passed as wastewater to a wastewater treatment or can be introduced in countercurrent into the preceding washing stage.

The washed nitroaromatic can either be fed into the subsequent washing stage or at the end of the wash be transferred directly to further processing or to intermediate storage.

As phase separation apparatus, it is possible to use all types of static separators but also dynamic separators such as centrifugal separators. The separation time for the nitroaromatic/washing medium emulsion depends not only on the type of emulsion (W/O or O/W) and the mixing energy introduced but also on the excess of base in the washing medium which is not required for neutralization. With introduction of the same mixing energy, the separation time decreases significantly with increasing base concentration in the washing medium. However, surface-active agents or mechanical separation aids, e.g. packings, separation plates, etc., can also be used to accelerate phase separation. The phase separation can also be accelerated by a spacing between the individual mixing elements which is matched to the nitroaromatic and type of emulsion.

As regards the crude nitrated products to be purified, these are generally liquid under process conditions, in particular at temperatures at or above 5° C., in particular at temperatures at or above 25° C., and atmospheric pressure. In particular, the crude nitrated products to be purified originate from the nitration of monocyclic or polycyclic aromatics, in particular from the nitration of benzene, toluene, xylene or halogenated aromatics such as, in particular, chlorinated benzenes.

The crude nitrated products to be purified are, in particular, optionally halogenated mononitroaromatics, dinitroaromatics and trinitroaromatics, e.g. nitrobenzene (MNB), mononitrotoluene (MNT), dinitrotoluene (DNT), trinitrotoluene (TNT), nitrochlorobenzene (MNCB) or the like.

In general, the process step (b) is followed by separation of the nitrated products which have been freed of the impurities from the washing medium. This separation is generally carried out by means of a suitable separation apparatus (separator or settler).

Furthermore, in a particular embodiment of the process of the invention, the mixture of purified nitrated products and washing medium leaving the tube reactor, in particular before the nitrated products which have been freed of the impurities have been separated off from the washing medium, can firstly be transferred into a stirred vessel. In this way, the contact and/or residence time between nitration products to be purified and washing medium is efficiently increased so that impurities which have not yet been washed out may be transferred into the washing medium or neutralized thereby.

In an advantageous embodiment of the process of the invention, the washing medium, in particular after the nitrated products which have been freed of the impurities have been separated off from the washing medium, is recycled. This makes efficient washing or circulation possible and reduces the amount of washing medium to a minimum.

Any residual amounts or traces of water still present, in particular suspended and/or dissolved water, can optionally be removed by drying from the purified nitroaromatic after the wash or after the washing medium has been separated off (e.g. after separation of the washing emulsion in a static separator or by means of a centrifugal separator).

The process of the invention is suitable for carrying out the acid wash and/or the basic wash and/or the neutral wash of the crude nitrated products. The process of the invention can thus be used in all three of the abovementioned washing steps. However, it is equally possible to use the process of the invention for only one or two washing stages, for example only for the acid wash or else only for the basic wash or else only for the neutral wash. In this respect, the process of the invention can be used flexibly.

As indicated above, the process of the invention is associated with a number of advantages and particular aspects, of which the following few advantages and particular aspects will be mentioned, but not exhaustively and not implying any restriction:

In particular, the process of the invention allows efficient purification of crude nitrated products obtained in the nitration of nitratable aromatic compounds after removal of the residual nitrating acid, with only a low complexity and good process economics, e.g. process efficiency.

The tube reactor used according to the invention makes efficient and intimate dispersion of washing medium and crude nitrated aromatics in one another possible, so that no further washing steps or other treatment steps are required. The washing or treatment efficiency can be increased further by additional mixing elements which, as indicated above, further improve mixing being provided in the tube reactor.

The tube reactor employed according to the invention for the purification can equally well be used as reaction vessel in the preceding nitration, so that no additional apparatus has to be used for the purification of the crude nitrated products.

The tube reactor employed according to the invention for the purification of the crude nitration products makes it possible to produce large exchange areas in a two-phase mixture of washing medium and crude nitrated aromatics, so that effective mass transfer and rapid transfer of the impurities into the washing medium, or in the case of acidic compounds rapid neutralization, are ensured in this way.

Furthermore, the process of the invention makes it possible for the impurities coming from the nitration to be removed rapidly and at the same time efficiently from the crude nitrated products, with the washing medium being able to be readily recycled or circulated after the treatment of the crude nitrated aromatics.

The present invention further provides, according to a second aspect of the present invention, an apparatus (plant) for removing impurities from crude nitrated products obtained in the nitration of nitratable aromatic compounds by treating the crude products, after removal of the residual nitrating acid, with a washing medium, where the apparatus of the invention is particularly suitable for carrying out a process as described above, wherein the apparatus has the following devices:
(a) at least one dispersing device, in particular at least one mixing device, for contacting and emulsifying crude nitrated products to be purified and washing medium; and,
(b) arranged downstream of the dispersing device, a tube reactor for introduction of the emulsion of crude nitrated products to be purified and washing medium produced in the dispersing device, where the tube reactor is configured so that removal of the impurities initially present in the crude nitrated products is made possible during passage of the emulsion through the tube reactor and/or that the impurities initially present in the crude nitrated products are transferred into the washing medium and/or neutralized thereby during passage of the emulsion through the tube reactor.

As indicated above in connection with the process of the invention, the dispersing device, in particular the mixing device, can be a stirred vessel, a jet mixer or a pump, in particular a centrifugal pump, preferably a pump, in particular a centrifugal pump, or a jet mixer, particularly preferably a jet mixer.

As indicated above in the context of the process of the invention, the dispersing device, in particular the mixing device, can be installed upstream of the reactor, in particular directly upstream. In particular, the dispersing device, in particular the mixing device, can in this case go over into the tube reactor.

In an alternative embodiment, the dispersing device, in particular the mixing device, can be integrated into the tube reactor and/or be a constituent of the tube reactor. In this regard, reference may be made to what has been said above in connection with the process of the invention.

As explained above in the description of the process of the invention, the tube reactor can be equipped with mixing elements, in particular for introduction of additional mixing energy. As described above, the mixing elements can be configured as plates, in particular impingement plates or deflection plates, as orifice plates, as static mixers or as flow dividers.

A single-stage, two-stage or three-stage wash of the crude nitration product (e.g. acid wash and/or basic wash and/or neutral wash) can be carried out in the apparatus of the invention.

Furthermore, it is possible, according to the invention, for a separation device, in particular a separator or settler and/or dynamic separator or centrifugal separator, to be arranged downstream of the tube reactor in order to separate off the nitrated products which have been freed of the impurities from the washing medium.

In addition, it is possible, in the apparatus of the invention, for a stirred vessel and/or stirred reactor to be arranged downstream of the tube reactor and upstream of the separation device (i.e. in other words between tube reactor and separation device). In particular, the contact and/or residence time between nitrated products and the washing medium is increased in this way.

For further details regarding the apparatus or plant of the invention, reference may be made to what has been said above in respect of the process of the invention, which applies analogously to the apparatus or plant of the invention.

Finally, the present invention further provides, according to a third aspect of the present invention, a production plant for nitrating nitratable aromatic compounds with subsequent purification of the crude nitrated products formed in the nitration, wherein the production plant comprises the following units:
(a) a nitration unit for nitrating aromatic compounds, in particular having one or more appropriate reaction vessels for carrying out the nitration reaction(s);
(b) optionally, arranged in the production line downstream of the nitration unit, at least one separation device, in particular a separator, for separating off the residual nitrating acid from the crude nitrated products;
(c) arranged in the production line downstream of the nitration unit and any separation device present, at least one washing device for carrying out washing of the crude nitrated products, where the washing device comprises:
at least one dispersing device, in particular at least one mixing device, for contacting and emulsifying the crude nitrated products to be purified and the washing medium and,
arranged downstream of the dispersing device, a tube reactor for introduction of the emulsion of crude nitrated products to be purified and washing medium produced in the dispersing device, where the tube reactor is configured so that removal of the impurities initially present in the crude nitrated products is made possible during passage of the emulsion through the tube reactor and/or that the impurities initially present in the crude nitrated products are transferred into the washing medium and/or neutralized thereby during passage of the emulsion through the tube reactor;
(d) optionally, arranged in the production line downstream of the washing device, a stirred vessel, in particular for increasing the contact and/or residence time between nitrated products and washing medium;
(e) arranged in the production line downstream of the washing unit and any stirred vessel present, a separation device, in particular a separator, for separating off the nitrated products which have been freed of the impurities from the washing medium.

In other words, in the production plant of the invention, the above-described apparatus or plant for purification, i.e. for removal of impurities, is a constituent of this production plant, namely in the form of the washing unit or washing device (c).

As indicated above, the dispersing device, in particular the mixing device, can be a stirred vessel, a jet mixer or a pump, in particular a centrifugal pump, preferably a pump, in particular a centrifugal pump, or a jet mixer, particularly preferably a jet mixer, in the production plant of the invention, too.

In a particular embodiment of the production plant of the invention, the dispersing device, in particular the mixing device, can, as indicated above, be installed upstream of the reactor, in particular directly upstream of the reactor. In this embodiment, the dispersing device, in particular the mixing device, can, in particular, go over into the tube reactor.

It is likewise possible according to the invention for the dispersing device, in particular the mixing device, to be integrated into the tube reactor and/or to be a constituent of the tube reactor. As regards this embodiment, reference may be made to what has been said above in order to avoid unnecessary repetition.

As indicated above in connection with the process of the invention and in connection with the purification apparatus or plant of the invention, the tube reactor can be equipped with mixing elements, in particular for introduction of additional mixing energy. In this embodiment, the mixing elements can, in particular, be configured as plates, in particular impingement plates or deflection plates, as orifice plates, as static mixers or as flow dividers.

The process of the invention is particularly suitable for carrying out an acid wash and/or a basic wash and/or a neutral wash of crude nitrated products. The process of the invention can thus be employed in all three abovementioned washing steps of a washing device. However, it is equally possible to use the process of the invention for only one or two washing steps, for example only for an acid wash or else only for a basic wash or else only for a neutral wash. In this respect, the process of the invention can be used flexibly.

For further details regarding the production plant of the invention, reference may be made to what has been said above in respect of the process of the invention and the apparatus or plant of the invention, with this applying analogously to the production plant of the invention.

The process of the invention and the apparatus or plant of the invention for purification and also the production plant according to the invention for nitration are illustrated by way of example and in a nonrestrictive manner in the attached figures.

Figure 2:
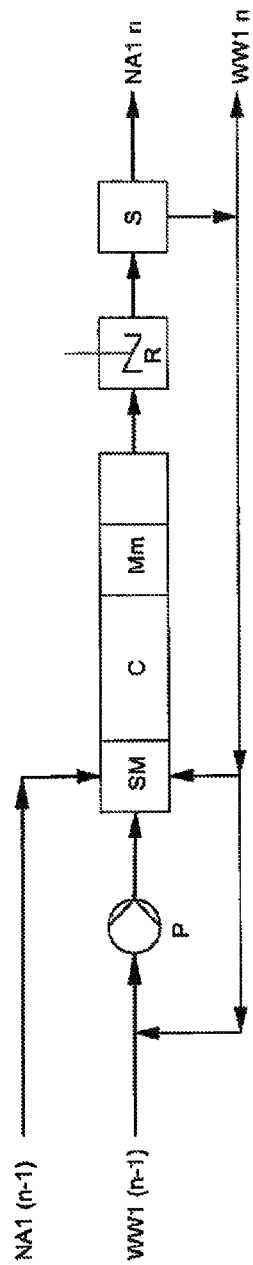
FIG. 2 provides a schematic depiction of a single-stage wash for nitroaromatics according to the process of the invention or using the apparatus or plant of the invention.
Figure 3:
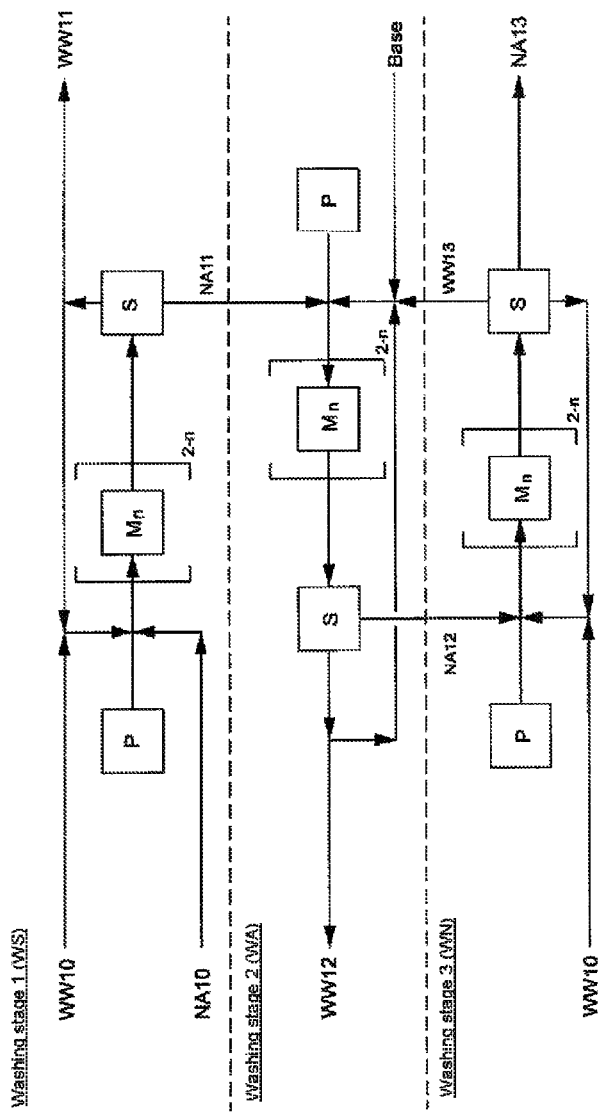
FIG. 3 provides a schematic flow diagram of the process of the invention or a schematic depiction of the apparatus or plant of the invention as per a preferred working example of the invention for the usual three washing stages of a wash of nitroaromatics.
Figure 4:
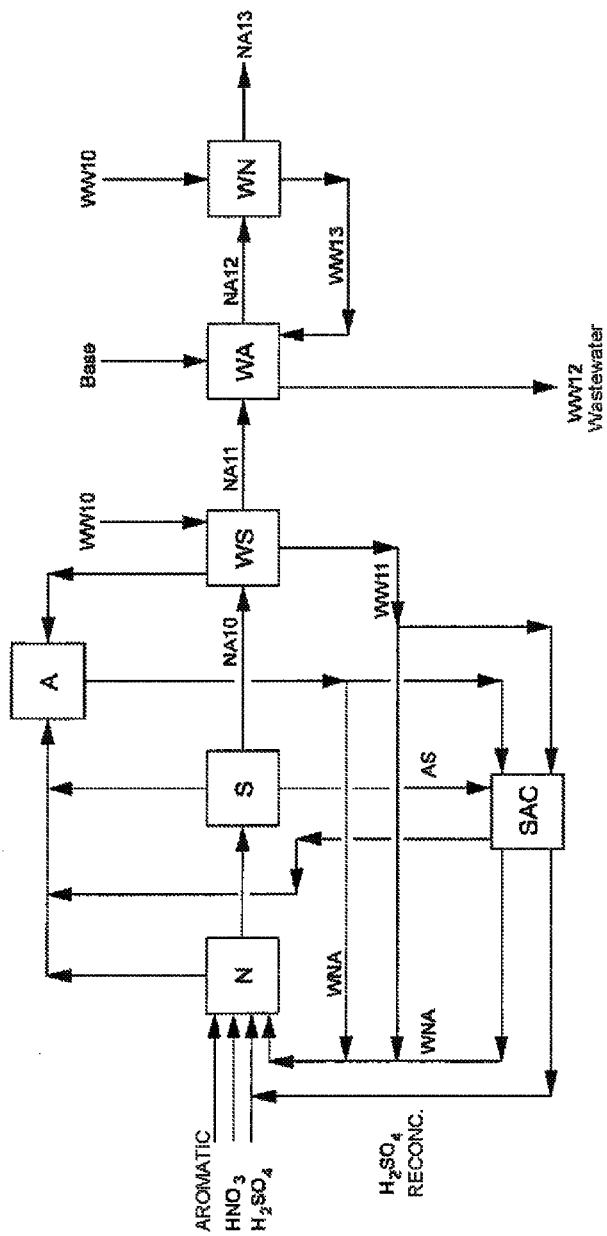
FIG. 4 provides a schematic depiction of a production plant according to the invention for nitrating nitratable aromatic compounds with subsequent washing of the resulting nitroaromatics as per a preferred working example of the invention.

Further advantages, properties, aspects and features of the present invention can be seen from the following description of embodiments which are preferred according to the invention and are shown in the drawings. The figures show:

FIG. 1 a schematic depiction of a wash of nitroaromatics according to the prior art by means of mixer/settler technology for the usual three washing stages of a wash of nitroaromatics;

FIG. 2 a schematic depiction of a single-stage wash for nitroaromatics according to the process of the invention or using the apparatus or plant of the invention;

FIG. 3 a schematic flow diagram of the process of the invention or a schematic depiction of the apparatus or plant of the invention as per a preferred working example of the invention for the usual three washing stages of a wash of nitroaromatics;

FIG. 4 a schematic depiction of a production plant according to the invention for nitrating nitratable aromatic compounds with subsequent washing of the resulting nitroaromatics as per a preferred working example of the invention.

FIG. 1 shows an example of a wash of nitroaromatics in three steps according to the prior art:

a) In step 1, the sulfuric acid and nitric acid suspended and dissolved in the crude nitroaromatic (NA 10) are washed out by washing with fresh water (WW 10) in a multistage continuous acid wash (WS). The nitroaromatic (NA 10) to be washed and the washing water (WW 10) are fed into a mixing device, usually a stirred vessel, having a residence time of about 10 minutes. The washing emulsion formed is subsequently separated in a separator (S). To completely remove the dissolved and suspended mineral acids, it is possible to use up to 4 mixer/settler units (n=3), with the washing medium and the nitroaromatic to be washed being conveyed in countercurrent. The washing medium is, after phase separation, either all discharged immediately as wastewater (WW 11) or part of it is additionally circulated in order to set a prescribed phase ratio and thus a defined type of emulsion and to minimize the time for separation of the phases. The nitroaromatic (NA 11) which has been freed of mineral acids is fed into washing stage 2, the alkaline wash (WA).

b) In step 2, all dissolved nitrophenols, nitrobenzoic acids and other acidic materials from the oxidative degradation of impurities and isomeric nitroaromatics are removed from the nitroaromatic (e.g. TNT) in a multistage continuous alkaline wash (WA). The nitroaromatic (NA 11) to be washed and the washing water (WW 10 or WW 13) are, together with a base, fed into a stirred vessel having a residence time of about 10 minutes. The washing emulsion formed is subsequently separated in a separator (S). To completely remove the nitrophenols, nitrobenzoic acids and other acidic materials from the oxidative degradation of impurities and isomeric nitroaromatics which are dissolved in the nitroaromatic, it is possible to use up to 4 mixer/settler units (n=3), with the washing medium and the nitroaromatic to be washed being conveyed in countercurrent. The washing medium is, after phase separation, either all discharged immediately as wastewater (WW 12) or part of it is additionally circulated in order to set a prescribed phase ratio and thus a defined type of emulsion and to minimize the time for separation of the phases. The nitroaromatic (NA 12) which has been freed of mineral acids, nitrophenols, nitrobenzoic acids and other acidic materials from the oxidative degradation of impurities and isomeric nitroaromatics is fed into washing stage 3, the neutral wash (WN).

c) In step 3, the entrained traces of washing medium from the alkaline wash (WA) are removed in a multistage neutral wash (WN). The nitroaromatic (NA 12) to be washed and the washing water (WW 10) are fed into a stirred vessel having a residence time of about 10 minutes. The washing emulsion formed is subsequently separated in a separator (S). To completely remove the traces of base still suspended or dissolved in the nitroaromatic, it is possible to use up to 4 mixer/settler units (n=3), with the washing medium and the nitroaromatic to be washed being conveyed in countercurrent. The aqueous phase is either all fed immediately as washing medium (WW 13) into the alkaline wash (WA) or part of it is additionally circulated in order to set a prescribed phase ratio and thus a defined type of emulsion and to minimize the time for separation of the phases.

The nitroaromatic (NA 13) which has now been freed of mineral acids, nitrophenols, nitrobenzoic acids and other acidic materials from the oxidative degradation of impurities, isomeric nitroaromatics and residual traces of alkali is passed on directly for further processing or to intermediate storage.

FIG. 2 shows an embodiment for one washing stage according to the process of the invention or in the apparatus or plant of the invention for washing nitroaromatics using the washing medium as driving jet.

The nitroaromatic to be washed is, after removal of the residual nitrating acid (NA1 (n−1) where n=1) or after removal of the residual nitrating acid still suspended as microemulsion in the nitroaromatic or of the sulfuric acid, nitric acid and nitrogen dioxide still dissolved in the nitroaromatic in an acid wash (WS with n=2) or after removal of all nitrophenols, nitrobenzoic acids and other acidic materials from the oxidative degradation of impurities and isomeric nitroaromatics dissolved in the nitroaromatic from the nitroaromatic (e.g. TNT) in the presence of bases in an alkaline wash (WA with n=3), combined in a jet mixer (SM) with the washing medium WW1 (n−1) which in the case shown serves as driving jet and introduced directly into a tube reactor (C) which contains additional mixing elements (Mm).

To set an increased residence time so as to permit slow reactions of the impurities to be washed out in the washing medium, e.g. nitrogen dioxide, the washing emulsion can be fed from the tube reactor into a residence vessel, e.g. one or more stirred vessels (R). The washing emulsion from the tube reactor is separated either directly or after a prolonged residence time in the stirred vessel into the phases in a separation device.

The washed nitroaromatic (NA1 n where n=1 to 3) is discharged either into the subsequent washing stage or as a finished washed product (NA13) for further processing. The loaded washing medium (WW1 n where n=1 to 3) is either discharged directly as wastewater or recirculated as substream to set a defined phase ratio between nitroaromatic and washing medium. This recirculated substream can be fed either together with the freshly added washing water as driving jet or as circulating stream directly into the tube reactor.

FIG. 3 shows an example of the process of the invention in three steps for the separate removal of the mineral acids by means of acid wash (WS), the removal of all dissolved nitrophenols, nitrobenzoic acids and other acidic materials from the oxidative degradation of impurities and isomeric nitroaromatics in the presence of bases in the alkaline range by means of an alkaline wash (WA) and a neutral wash (WN).

a) In step 1, the sulfuric acid and nitric acid suspended and dissolved in the crude nitroaromatic (NA 10) are removed by washing with fresh water (WW 10) in a single-stage acid wash (WS). The nitroaromatic (NA 10) to be washed and the washing water (WW 10) are fed by means of pumps (P) either via a jet mixer or directly into a tube reactor containing additional mixing elements (Mn). After passing through the tube reactor, the emulsion formed is separated in a separator (S). The washing medium is, after phase separation, either discharged directly as wastewater (WW 11) or part of it is additionally circulated for setting a prescribed phase ratio and thus a defined type of emulsion and to minimize the time for separation of the phases. The nitroaromatic (NA 11) which has been freed of mineral acids is fed into washing stage 2, the alkaline wash (WA).

b) In step 2, all dissolved nitrophenols, nitrobenzoic acids and other acidic materials from the oxidative degradation of impurities and isomeric nitroaromatics are removed from the nitroaromatic in a single-stage alkaline wash (WA). The nitroaromatic (NA 11) to be washed coming from the acid wash (WS) and the washing water (WW 10 or WW 13 from the neutral wash) and a base are fed by means of pumps (P) either via a jet mixer or directly into a tube reactor containing additional mixing elements (Mn). After passing through the tube reactor, the emulsion formed is separated in a separator. The washing medium, which contains all dissolved nitrophenols, nitrobenzoic acids and other acidic materials from the oxidative degradation of impurities and extracted isomeric nitroaromatics (dissolved as salt), is, after phase separation, either discharged directly as wastewater (WW 12) or part of it is circulated to set a prescribed phase ratio and thus a defined type of emulsion and to minimize the time for separation of the phases. The nitroaromatic (NA 12) which has been freed of mineral acids, nitrophenols, nitrobenzoic acids and other acidic materials from the oxidative degradation of impurities and isomeric nitroaromatics is fed into washing stage 3, the neutral wash (WN).

c) In step 3, the entrained traces of washing medium from the alkaline wash are removed in a single-stage neutral wash (WN). The nitroaromatic (NA 12) to be washed and the washing water (WW 10) are fed by means of pumps (P) either via a jet mixer or directly into a tube reactor containing additional mixing elements (Mn). After passing through the tube reactor, the emulsion formed is separated in a separator (S). The washing medium, which contains the residual traces of alkali and impurities, is either introduced directly as wastewater (WW 13) into the washing stage 2 (WA) or part of it is additionally circulated to set a prescribed phase ratio and thus a defined type of emulsion and to minimize the time for separation of the phases. The nitroaromatic (NA 13) which has now been freed of mineral acids, nitrophenols, nitrobenzoic acids and other acidic materials from the oxidative degradation of impurities, isomeric nitroaromatics and residual traces of alkali is passed directly to further processing or to intermediate storage.

FIG. 4 shows an example of a production plant for preparing nitroaromatics which has an integrated wash according to the invention of the crude nitroaromatics from an isothermal or adiabatic nitration. The crude nitroaromatic (NA 10) formed in the nitration unit (N) by reaction of the aromatic with nitric acid in the presence of sulfuric acid is, after removal of the nitrating acid in the separator (S), washed with water (WW 10) in the manner according to the invention in the acid wash (WS). After phase separation, the resulting wastewater (WW 11), which contains all washed-out sulfuric acid and nitric acid, is recirculated together with the nitric acid (WNA) obtained from the offgas treatment of the nitration plant in an absorber plant (A), either directly or after concentration in an SAC plant (SAC), together with the residual acid (AS) from the nitration back to the nitration or discharged as wastewater to be treated.

The nitroaromatic (NA 11) which has been freed of the mineral acids is washed in effect in one stage in the presence of bases by the process of the invention in the washing stage 2 (alkaline wash WA). After phase separation, the wastewater from the alkaline wash (WW12), which has a pH in the range from 8.0 to 13 and contains all nitrophenols, nitrobenzoic acids and other acidic materials from the oxidative degradation of impurities and isomeric nitroaromatics (e.g. TNT), is fed to an additional treatment, e.g. a thermolysis, before discharge into a main outfall.

The nitroaromatic (NA 12) from the alkaline wash (WA) is fed into the neutral wash (WN) and washed with water (WW 10) in effect in one stage by the process of the invention. After phase separation, the wastewater (WW 13) from the neutral wash (WN) is fed together with base into the washing stage 2 (WA). The washed nitroaromatic (NA 13) is passed to further processing, e.g. to isomer separation or reduction to the corresponding amine, or to intermediate storage.

Further embodiments, modifications and variations of the present invention can be readily recognized and realized by a person skilled in the art on reading the description, without going outside the scope of the present invention.

The present invention is illustrated with the aid of the following working examples, but without the present invention being restricted thereto.

Even though, in the following working examples, the process of the invention or the apparatus of the invention is illustrated using nitrobenzene as nitroaromatic to be purified, the process or the apparatus of the present invention is in no way restricted thereto but can also be applied to any other nitroaromatics, e.g. from the nitration of toluene, chlorobenzenes, xylenes, nitrobenzenes, etc., and to any bases other than sodium hydroxide.

WORKING EXAMPLES

Example 1

Single-Stage Alkaline Wash (Comparative Example)

12 kg/h of a nitrobenzene from an adiabatic nitration, which had been prewashed with water (acid wash) and still contained a total of 1910 ppm of nitrophenols (0.8 ppm of 2-nitrophenol (2-NP), 1346 ppm of 2,4-dinitrophenol (2,4-DNP) and 203 ppm of 2,6-dinitrophenol (2,6-DNP) and 360 ppm of picric acid (2,4,6-TNP)), was fed together with a washing liquor containing 0.8 g of NaOH/l (two-fold excess, based on all nitrophenols) in a weight ratio of 1:1 into a stirred vessel at 60° C. The stirrer speed was set so that an O/W emulsion having the phase ratio as metered in was present in the stirred vessel. The residence time in the stirred vessel was 6 minutes. After phase separation (about 40 minutes), the pH of the washing liquor, which contained 1850 ppm of nitrophenols, was about 11.7. 60 ppm of nitrophenols were found in the washed nitrobenzene. When a washing liquor containing 4 g/l of sodium hydroxide was used under otherwise identical conditions, the separation time could be shortened by a factor of virtually 4 to about 15 minutes.

Example 2

Single-Stage Alkaline Wash (According to the Invention)

12 kg/h of a nitrobenzene from an adiabatic nitration, which had been prewashed with water (acid wash) and still contained a total of 1910 ppm of nitrophenols (0.8 ppm of 2-nitrophenol (2-NP), 1346 ppm of 2,4-dinitrophenol (2,4-DNP) and 203 ppm of 2,6-dinitrophenol (2,6-DNP) and 360 ppm of picric acid (2,4,6-TNP)), was fed together with a washing liquor containing 0.8 g of NaOH/l (two-fold excess, based on all nitrophenols) in a weight ratio of 1:1 by means of a jet mixer using the washing medium as central jet at 60° C. into a tube reactor which additionally contained 5 static mixing elements. The relative velocity between central jet and nitrobenzene to be washed was 8:1. The residence time in the tube reactor was not more than 5 seconds. The pressure drop over the entire length of the tube reactor was 1.6 bar. After phase separation of the O/W emulsion (about 40 minutes), the pH of the washing liquor, which contained 1908 ppm of nitrophenols, was about 11.6. 2 ppm of nitrophenols were found in the washed nitrobenzene. When a washing liquor containing 4 g/l of sodium hydroxide was used under otherwise identical conditions, the separation time could be shortened by a factor of 4 to about 10 minutes. The same results were achieved using the nitroaromatic to be washed as central jet in the jet mixer.

Example 3

Single-Stage Neutral Wash (According to the Invention)

12 kg/h of a nitrobenzene from an adiabatic nitration, which after washing with alkali (see, for example, example 2, alkaline wash) still contained a total of from 2 to 5 ppm of nitrophenols, was fed in a weight ratio of 1:1 by means of a jet mixer using water as central jet at 60° C. into a tube reactor which additionally contained 2 static mixing elements. The relative velocity between central jet and nitrobenzene to be washed was 8:1. The residence time in the tube reactor was about 5 seconds. The pressure drop over the entire length of the tube reactor was 0.6 bar. After phase separation (about 25 minutes), the pH of the washing water containing from about 1.5 to 4.5 ppm of nitrophenols was about 9.0. 0.5 ppm of nitrophenols was still found in the washed nitrobenzene. The same results were achieved using the nitroaromatic to be washed as central jet in the jet mixer.

Example 4

Single-Stage Alkaline Wash (According to the Invention)

20 kg/h of a nitrobenzene from an adiabatic nitration, which had been prewashed with water (acid wash) and still contained a total of 1910 ppm of nitrophenols (0.8 ppm of 2-nitrophenol (2-NP), 1346 ppm of 2,4-dinitrophenol (2,4-DNP) and 203 ppm of 2,6-dinitrophenol (2,6-DNP) and 360 ppm of picric acid (2,4,6-TNP)), was washed directly with 4 kg/h of washing liquor containing 4 g of NaOH/l (two-fold excess, based on all nitrophenols), corresponding to a weight ratio of nitroaromatic to washing liquor of 5:1, with the washing medium being fed by means of a jet mixer and the nitroaromatic to be washed at 60° C. into a tube reactor which additionally contained 5 static mixing elements. The relative velocity between central jet and nitrobenzene to be washed was 8:1. The residence time in the tube reactor was not more than 5 seconds. The pressure drop over the entire length of the tube reactor was 1.6 bar. After phase separation of the emulsion of the W/O type (about 5 minutes), the pH of the washing liquor, which contained 9552 ppm of nitrophenols, was about 12.3. About 8 ppm of nitrophenols were found in the washed, still turbid nitrobenzene.

Example 5

Single-Stage Neutral Wash (According to the Invention)

20 kg/h of a nitrobenzene from an adiabatic nitration, which after washing with alkali (see example 2, alkaline wash) still contained a total of from 5 to 8 ppm of nitrophenols, was fed in a weight ratio of 5:1 by means of a jet mixer using water as central jet at 60° C. into a tube reactor which additionally contained 2 static mixing elements. The relative velocity between central jet and nitrobenzene to be washed was 8:1. The residence time in the tube reactor was about 5 seconds. The pressure drop over the entire length of the tube reactor was 0.6 bar. After phase separation (about 20 minutes), the pH of the washing water containing from about 1.5 to 4.5 ppm of nitrophenols was about 9.0. 0.5 ppm of nitrophenols was still found in the washed nitrobenzene. The same results were achieved using the nitroaromatic to be washed as central jet in the jet mixer.

The invention claimed is:
1. A production plant for nitrating nitratable aromatic compounds with subsequent purification of the crude nitrated products formed in the nitration,
wherein the production plant comprises the following units:

(a) a nitration unit for nitrating aromatic compounds, wherein the nitration unit comprises one or more appropriate reaction vessels for carrying out the nitration reaction(s);

(b) optionally, arranged in the production line downstream of the nitration unit, at least one separation device for separating off the residual nitrating acid from the crude nitrated products;

(c) arranged in the production line downstream of the nitration unit and the optional separation device if present, at least one washing device for carrying out washing of the crude nitrated products, where the washing device comprises:

at least one dispersing device for contacting and emulsifying the crude nitrated products to be purified and the washing medium, and, arranged downstream of the dispersing device, a tube reactor for introduction of the emulsion comprising the crude nitrated products to be purified and the washing medium and produced in the dispersing device, wherein the tube reactor is configured such that the impurities initially present in the crude nitrated products are removed during passage of the emulsion through the tube reactor and/or such that the impurities initially present in the crude nitrated products are transferred into the washing medium and neutralized thereby during passage of the emulsion through the tube reactor, wherein the tube reactor is equipped with one or more mixing elements for introduction of additional mixing energy, wherein the mixing elements are configured as plates, as impingement plates, as deflection plates, as orifice plates, as static mixers or as flow dividers;

(d) optionally, arranged in the production line downstream of the washing device, a stirred vessel for increasing the contact and residence time between nitrated products and washing medium;

(e) arranged in the production line downstream of the washing device and the optional stirred vessel if present, a separation device for separating off the nitrated products which have been freed of the impurities from the washing medium.

2. The production plant as claimed in claim 1, wherein the dispersing device is a jet mixer or a centrifugal pump.

3. The production plant as claimed in claim 1, wherein the dispersing device is installed upstream of the reactor, with the dispersing device going over into the tube reactor or being integrated into the tube reactor as a constituent of the tube reactor.

4. The production plant as claimed in claim 1, wherein the mixing elements are configured such to provide a mixing energy of from 10 to 1,000 joule/liter.

5. The production plant as claimed in claim 1, wherein the mixing elements are configured such to provide a pressure drop per mixing element in the range from 0.1 bar to 3.0 bar.

6. A production plant for nitrating nitratable aromatic compounds with subsequent purification of the crude nitrated products formed in the nitration, wherein the production plant comprises the following units:

(a) a nitration unit for nitrating aromatic compounds, wherein the nitration unit comprises one or more appropriate reaction vessels for carrying out the nitration reaction(s);

(b) optionally, arranged in the production line downstream of the nitration unit, at least one separation device for separating off the residual nitrating acid from the crude nitrated products;

(c) arranged in the production line downstream of the nitration unit and the optional separation device if present, at least one washing device for carrying out washing of the crude nitrated products, where the washing device comprises:

at least one dispersing device for contacting and emulsifying the crude nitrated products to be purified and the washing medium, and arranged downstream of the dispersing device, a tube reactor for introduction of the emulsion comprising the crude nitrated products to be purified and the washing medium and produced in the dispersing device, wherein the tube reactor is configured such that the impurities initially present in the crude nitrated products are removed during passage of the emulsion through the tube reactor and/or such that the impurities initially present in the crude nitrated products are transferred into the washing medium and neutralized thereby during passage of the emulsion through the tube reactor, wherein the tube reactor is equipped with one or more mixing elements for introduction of additional mixing energy, wherein the mixing elements are configured as plates, as impingement plates, as deflection plates, as orifice plates, as static mixers or as flow dividers and wherein the mixing elements are configured such to provide a mixing energy of from 10 to 1,000 joule/liter;

(d) optionally, arranged in the production line downstream of the washing device, a stirred vessel for increasing the contact and residence time between nitrated products and washing medium;

(e) arranged in the production line downstream of the washing device and the optional stirred vessel if present, a separation device for separating off the nitrated products which have been freed of the impurities from the washing medium.

7. A production plant for nitrating nitratable aromatic compounds with subsequent purification of the crude nitrated products formed in the nitration, wherein the production plant comprises the following units:

(a) a nitration unit for nitrating aromatic compounds, wherein the nitration unit comprises one or more appropriate reaction vessels for carrying out the nitration reaction(s);

(b) optionally, arranged in the production line downstream of the nitration unit, at least one separation device for separating off the residual nitrating acid from the crude nitrated products;

(c) arranged in the production line downstream of the nitration unit and the optional separation device if present, at least one washing device for carrying out washing of the crude nitrated products, where the washing device comprises:

at least one dispersing device for contacting and emulsifying the crude nitrated products to be purified and the washing medium, and, arranged downstream of the dispersing device, a tube reactor for introduction of the emulsion comprising the crude nitrated products to be purified and the washing medium and produced in the dispersing device, wherein the tube reactor is configured such that the impurities initially present in the crude nitrated products are removed during passage of the emulsion through the tube reactor and/or such that the impurities initially present in the crude nitrated products are transferred into the washing medium and neutralized thereby during passage of the emulsion through the tube reactor, wherein the tube reactor is equipped with one or more mixing elements for introduction of additional mixing energy, wherein the mixing elements are configured as plates, as impingement plates, as deflection plates, as orifice plates, as static mixers or as flow dividers and wherein the mixing elements are configured such to provide a pressure drop per mixing element in the range from 0.1 bar to 3.0 bar;

(d) optionally, arranged in the production line downstream of the washing device, a stirred vessel for increasing the contact and residence time between nitrated products and washing medium;

(e) arranged in the production line downstream of the washing device and the optional stirred vessel if present, a separation device for separating off the nitrated products which have been freed of the impurities from the washing medium.

\* \* \* \* \*